United States Patent [19]

Chiu et al.

[11] Patent Number: 5,587,926
[45] Date of Patent: Dec. 24, 1996

[54] REFRIGERATED FLUID SAMPLING APPARATUS AND METHOD WITH VARIABLE VOLUME SAMPLING SYSTEM

[75] Inventors: Francis Chiu, Amherst; William Goss, Buffalo; David Hayes, North Tonawanda; Gary Randolph; Cheryl Sak, both of Lyndonville; Jeff Valery, Lockport; James Vineski, Bergen, all of N.Y.

[73] Assignee: American Sigma, Inc., Medina, N.Y.

[21] Appl. No.: 348,050

[22] Filed: Dec. 1, 1994

Related U.S. Application Data

[63] Continuation-in-part of Ser. No. 219,097, Mar. 29, 1994, Pat. No. 5,506,791, which is a continuation-in-part of Ser. No. 954,288, Sep. 30, 1992, Pat. No. 5,299,141, which is a continuation-in-part of Ser. No. 612,832, Nov. 13, 1990, Pat. No. 5,172,332, which is a continuation-in-part of Ser. No. 455,981, Dec. 22, 1989, Pat. No. 5,091,863.

[51] Int. Cl.$^6$ .................................................. G01F 11/00
[52] U.S. Cl. ............................................................ 364/510
[58] Field of Search ........................................ 364/509, 510; 73/863.01, 863, 863.02, 863.03, 863.34; 141/1, 89, 91, 94, 130; 422/82.11, 98; 385/12

[56] References Cited

U.S. PATENT DOCUMENTS 5,299,141  3/1994  Hungerford et al. .................... 364/510
5,506,791  4/1996  Hungerford et al. .................... 364/510

Primary Examiner—Ellis B. Ramirez
Attorney, Agent, or Firm—Weiner, Carrier & Burt, P.C.; William F. Esser; Irving M. Weiner

[57] ABSTRACT

A refrigerated automatic fluid sampling apparatus having a compressor assembly mounted in an upper portion thereof, above the thermally-controlled sample compartment. The apparatus includes a thermal control system which prolongs compressor life and optimizes compressor operation by exercising the compressor assembly during prolonged periods of non-use, preventing short-cycling of the compressor, and accurately monitoring sample temperatures to minimize compressor starts. The invention further includes a sampling control system which employs a statistical regression model to simulate real-life pumping system and operating characteristics so as to accurately deliver a predetermined sample volume, which permits sampling on a constant time, variable volume basis as well as other sampling modes.

26 Claims, 11 Drawing Sheets

| FIG. 5A | FIG. 5B |

REFRIGERATED FLUID SAMPLING APPARATUS AND METHOD WITH VARIABLE VOLUME SAMPLING SYSTEM

This is a continuation-in-part of application Ser. No. 219,097 filed Mar. 29, 1994, now U.S. Pat. No. 5,506,791 which is in turn a continuation-in-part of application Ser. No. 954,288 filed Sep. 30, 1992 which issued as U.S. Pat. No. 5,299,141; which is in turn a continuation-in-part of application Ser. No. 612,832 filed Nov. 13, 1990 which issued as U.S. Pat. No. 5,172,332; which is in turn a continuation-in-part of application Ser. No. 455,981 filed Dec. 22, 1989 which issued as U.S. Pat. No. 5,091,863. The disclosure of each of such applications and patents is incorporated herein by reference thereto.

BACKGROUND OF THE INVENTION

1. Field of the Invention

The present invention relates generally to a refrigerated automatic fluid sampling apparatus having a top-mounted compressor assembly to enhance thermal efficiency and corrosion resistance, a thermal control system which optimizes compressor operation, and a sampling control system which uses a computer-simulated statistical model to deliver desired sample volumes with precision.

More particularly, the invention relates to a microprocessor-controlled refrigerated sampling apparatus with a weather-resistant external housing having a thermally-controlled sample compartment provided in a lower portion thereof, and a controller unit and compressor assembly mounted in an upper portion thereof. The controller unit includes a computer control means connected with a sample pumping system and a thermal control system for the compressor assembly. The thermal control system exercises the compressor assembly during periods of non-use, prevents short cycling of the compressor, and employs a unique sensor for accurately monitoring sample temperatures so as to minimize compressor starts. The sampling control system uses a statistical model to simulate the real-life pumping system and operating characteristics, permitting accurate delivery of a preselected sample volume.

2. Description of Relevant Art

To preserve sample integrity during the wastewater sample collection process, it is often necessary to refrigerate collected samples to prevent chemical and biological degradation due to ambient temperature extremes. Under current Environmental Protection Agency ("EPA") regulations, wastewater samples are required to be maintained at 4° C.

In known refrigerated sampler devices, the compressor is mounted at the bottom of the unit, near the floor and below the sample compartment. This known arrangement has a number of disadvantages. The bottom mounted compressor is not only inconveniently located for servicing, the heat generated by the compressor rises up and around the sample compartment, forcing the system to work harder. Further, bottom mounted compressors are exposed to the effects of highly corrosive heavier-than-air gases, such as chlorine and hydrogen sulfide, by-products of wastewater which hug the floor. Because the floors and walkways within waste treatment plants are regularly hosed down, bottom mounted compressors and associated refrigeration components are subjected to splatter and spray which accelerates the corrosion process.

The refrigerated sampling apparatus according to the present invention overcomes the problems associated with known bottom-mounted compressor arrangements by mounting the compressor assembly at the top of the unit, above the sample compartment. The top mounted compressor assembly of the invention not only lends itself to convenient servicing, it permits heat generated by the compressor to be vented away from the sample compartment to promote efficient cooling. Further, because the compressor is well above floor level, it is protected from the corrosive effects of heavier-than-air gases, hose spray and splatter, and the like.

The present invention also provides for flow-proportional variable sample volumes, which has heretofore been unavailable in automatic fluid sampling devices. Because fluid samples represent the source stream better when collected in proportion to the source stream flow rate, many federal and state discharge permits require that samples be collected in proportion to flow. While known automatic fluid sampling devices are capable of collecting fixed-volume samples at time intervals which vary proportionally with flow rate, they are incapable of varying the actual sample volume in proportion to flow rate. Known "variable time, constant volume" sampling devices are thus inherently incapable of providing the "constant time, variable volume" sampling called for by some discharge permits.

SUMMARY OF THE INVENTION

The invention provides a refrigerated fluid sampling apparatus comprising a main housing; a sample compartment disposed in a lower portion of the main housing; and fluid sampling means, disposed in the main housing, for withdrawing fluid from a fluid channel and delivering fluid samples to the sample compartment. Thermal control means are provided for controlling temperatures within the sample compartment, the thermal control means comprising a compressor assembly which is disposed in an upper portion of the main housing, above the sample compartment.

According to a preferred embodiment of the invention, control means comprising a microprocessor which controls the entire apparatus is also disposed in the upper portion of the main housing, forwardly of the top-mounted compressor assembly. The thermal control means comprises thermal controller interface circuitry connected with the main control means so as to transmit signals thereto and therefrom. The thermal control means further comprises first sensor means for sensing temperatures in the sample compartment which are representative of actual sample temperatures, the first sensor means being connected with the thermal controller interface circuitry. The first sensor means comprises a thermal mass substantially equivalent to a predetermined quantity of water, with signals therefrom being transmitted and processed by the thermal controller interface circuitry and the control means to control operation of the compressor assembly. Signals from the first sensor means further control operation of an evaporator heater which is also connected with the main control means via the thermal controller interface circuitry.

Preferably, the first sensor means of the thermal control means comprises a sensor casing constructed and dimensioned to simulate a glass beaker holding substantially 150 ml of water, with a thermistor being embedded in substantially the center of the thermal mass. In the preferred embodiment, the thermistor is of the Negative Temperature Coefficient type.

Also according to a preferred embodiment of the invention, program memory of the control means stores a thermal control algorithm for operating the compressor assembly at given time intervals to exercise same during prolonged periods of non-use. The control means is further provided with short cycle timing means for preventing the compressor assembly from being operated within a predetermined interval of time following the last operation thereof.

The invention further provides a sampling control system for an automatic fluid sampling apparatus having a pump with an inlet adapted to communicate with a supply of fluid to be sampled, and a control means including a microprocessor and program memory. The sampling control system comprises sensing means disposed at the input side of the pump for producing at least one signal related to the flow rate of fluid at the input side of the pump, and means for transmitting such signal to the control means. The microprocessor receives at least one signal and utilizes the program memory to calculate the flow rate at the input side of said pump. The program memory stores a statistical regression model for predicting the flow rate at the output side of the pump on the basis of the calculated value of the input side flow rate and a plurality of independent variables associated with operation of the pump. The program memory further stores at least one equation for computing the length of time the pump must operate to deliver a predetermined volume of fluid, based on the predicted flow rate at the output side of the pump.

In a preferred embodiment of the sampling control system of the invention, constant-time, time, variable-volume sampling is provided on the basis of user input parameters relating to flow characteristics of the fluid stream or discharge to be sampled and the desired total sample volume and collection time, and an algorithm for calculating the flow-proportional volumes of individual samples to be collected.

It is an object of the invention to provide a top-mounted compressor arrangement which permits heat generated by the compressor to be vented away from the sample compartment so as to enhance cooling efficiency, while at the same time protecting the compressor from corrosive materials located at floor level.

A further object of the invention is to provide a novel thermal control system which exercises the compressor assembly during periods of non-use, prevents compressor short cycling, and employs a novel sensor for accurately monitoring sample temperatures so as to minimize compressor starts.

Yet another object of the invention is to provide a sampling control system based on a statistical model which simulates a real-life pumping system and operating characteristics so as to accurately deliver a predetermined quantity of sample into a receiving container.

The above and further objects, details and advantages of the invention will become apparent from the following detailed description, when read in conjunction with the accompanying drawings.

DETAILED DESCRIPTION OF PREFERRED EMBODIMENTS

With reference to FIGS. 1–4, the refrigerated fluid sampling apparatus according to the invention is shown as comprising a main housing or cabinet 1 having a sample compartment 2 provided in a lower portion thereof and a controller unit 3 mounted in an upper portion thereof. Cabinet 1 is preferably fabricated of a material which is capable of withstanding extreme environmental temperatures and conditions, such as, for example, resin transfer-molded fiberglass with an ultraviolet-inhibiting laminate. A hinged, front-opening door 2A provides access to sample compartment 2, while a hinged, top-opening door 3A provides access to the controller unit 3 while protectively enclosing controller unit 3 when it is not being used.

By way of example, the dimensions of cabinet 1 may be approximately 28" (71 cm) wide, 28" (71 cm) deep, and 49" (125 cm) high. Because controller unit 3 is mounted in the upper portion of cabinet 1, it is conveniently disposed at approximately waist height of a user standing next to cabinet 1.

Figure 3:
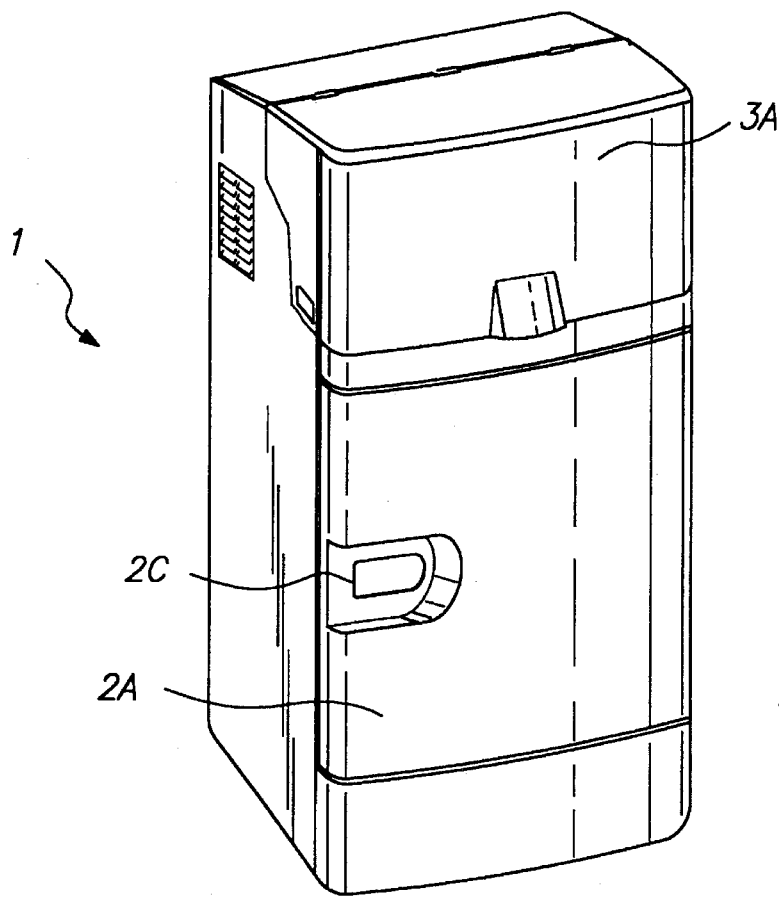
FIG. 3 is a perspective view of the apparatus of FIG. 1, with the controller compartment and sample compartment doors shown in a closed position.

The sample compartment 2 preferably has a double-walled construction with insulation, e.g., with two-inch thick foam insulation, while the door 2A is provided with a peripheral compressible gasket 2B, such that compartment 2 is sealed and insulated from the ambient when door 2A is closed and door latch 2C is latched. When cabinet 1 is in its entirely closed condition as shown in FIG. 3, it is sufficiently rugged to withstand harsh ambient weather conditions year-round.

Figure 1:
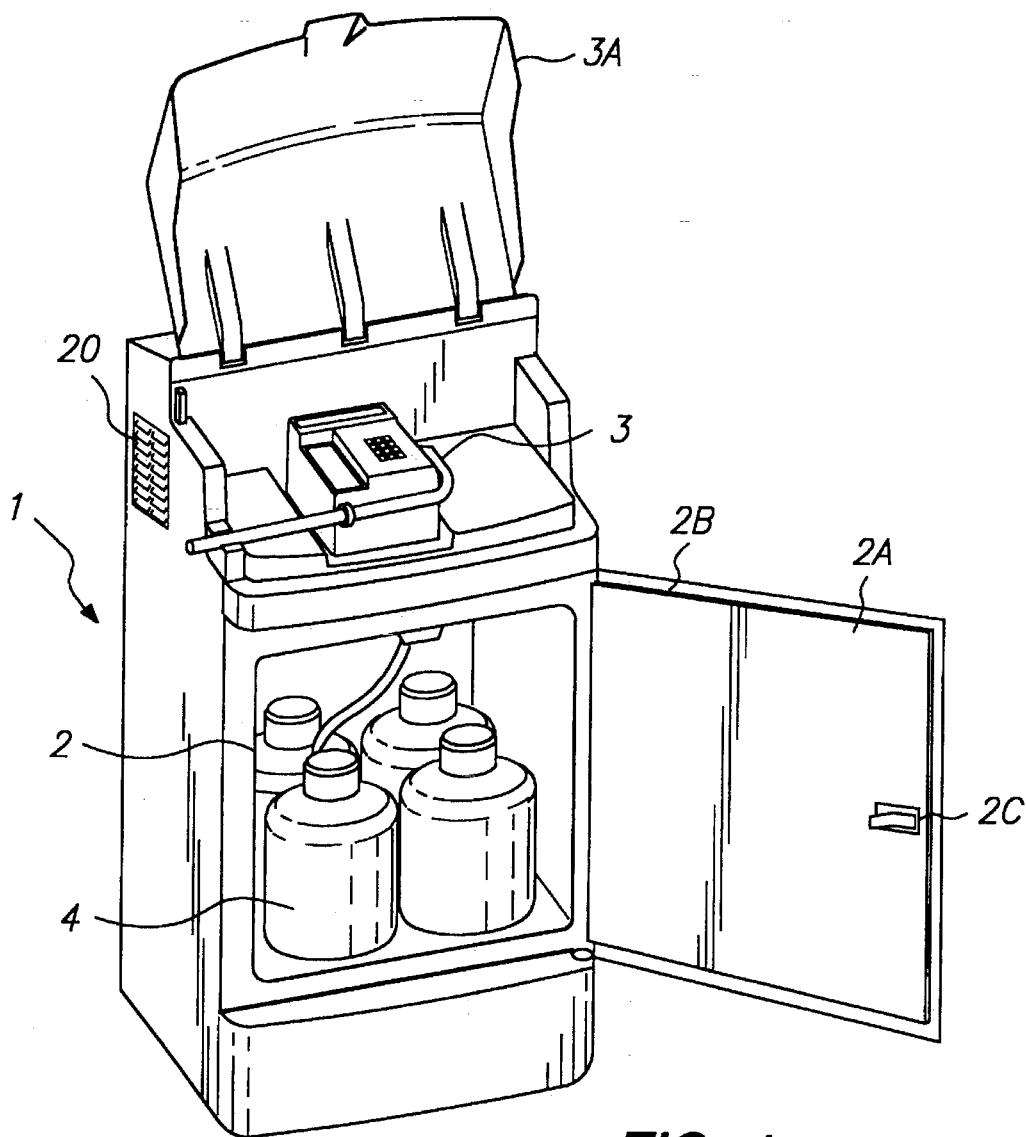
FIG. 1 is a perspective view of a refrigerated fluid sampling apparatus according to the invention, with the controller compartment and sample compartment doors shown in an open position.

Sample containers 4 are shown in FIG. 1 in the form of four three-gallon containers made of polyethylene or glass. It will be understood, however, that any number of sample containers ranging from only one to a multiplicity thereof, in varying sizes, may be employed within sample compartment 2, as desired. A suitable support means and distributor assembly (not shown) may be employed as needed for positioning sample containers within compartment 2 and for distributing fluid thereto.

Figure 4:
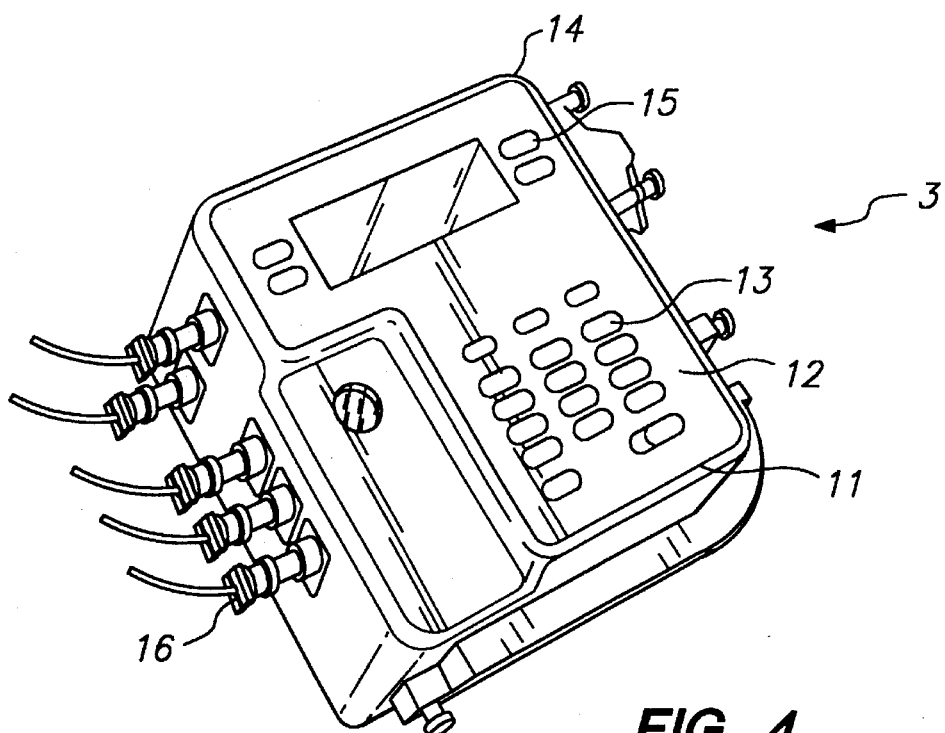
FIG. 4 is a perspective view of a controller unit of the apparatus according to the invention.

As shown in FIG. 4, the controller unit 3 of the invention comprises a case 11 which is preferably fabricated of a rugged thermoplastic material, such as ABS plastic, so that it too will withstand harsh conditions. The front portion of case 11 includes an operating panel 12 provided with a sealed membrane switch numeric keypad 13 for user input, a liquid crystal graphics/alphanumeric display 14, push buttons 15 for selectively operating display 14, and ON/OFF switches. The case 11 including operating panel 12 is completely sealed so as to be watertight, with added protection of operating panel 12 being afforded by fastening door 3A in a closed position. However, even when door 3A is open, the controller unit case 11 with the components mounted therein is watertight, dust-tight, and corrosion and ice resistant, conforming to NEMA 4X, 6 standards.

The controller unit 3 includes computer control means comprising a microprocessor which performs all mathematical and control functions required to operate the apparatus, with keypad 13 defining the interface which allows the user to program the apparatus and monitor its operation. A real-time clock provides the computer control means with access to current time and date information, so that events occurring during program execution may be recorded with corresponding time and date of occurrence.

Mounted on a side portion of case 11 are a plurality of external connectors 16 which preferably are each provided with a removable cap to protect same when not in use, although the connectors 16 are sealed in a watertight manner even without the caps. As described below, connectors 16 are adapted to have various devices connected thereto, including flow sensor(s), fluid condition monitoring sensor(s), a rain gauge, a power source such as a battery, a data transfer unit, etc. It will be understood that the number and type of connectors 16 may be varied as desired to accommodate a desired number and/or various types of sensors and external devices.

Various types of external devices which may be selectively linked with the apparatus of the invention via various ones of connectors 16 are described in the aforesaid copending U.S. patent application Ser. No. 219,097. By way of example, the apparatus of the invention may be selectively connected with: a pump so as to initiate sampler operation when water level rises above a predetermined level; a rain gauge so as to log data therefrom; a power source such as a battery; a data transfer unit etc. To this end, suitable external device interface electronics are connected with the microprocessor of the apparatus, and suitable programming is provided, to permit the apparatus to send control signals to the external device(s) as well as to receive and record data from same.

The apparatus of the invention may also provide fluid monitoring capabilities in substantially the same manner as described in the aforesaid U.S. Pat. No. 5,172,332, by attaching an appropriate fluid condition sensor to one of the external connectors 16 of controller unit 3. These monitoring capabilities enable the apparatus to calculate the value of a given fluid condition on the basis of inputs from a fluid condition sensor. By way of example, such fluid conditions may include pH level, oxidation reduction potential ("ORP"), temperature, solution conductivity or resistivity, dissolved oxygen, etc.

The apparatus of the invention is also preferably provided with automatic sampling features similar to those disclosed in the aforesaid U.S. Pat. Nos. 5,091,863 and/or 5,172,332. For example, the user may instruct the apparatus, via keypad 13, to initiate sampling operations on the basis of a fluid flow related variable, or on the basis of high, low, or a range of critical levels of fluid condition(s) as calculated by the microprocessor on the basis of inputs from a fluid condition monitoring sensor. Upon user request, the apparatus of the invention also automatically calculates and stores fluid flow-related variables and levels of fluid conditions to permit tracking of the history of the fluid conditions in a process stream. Likewise, the temperatures of samples within sample compartment 2 are automatically stored upon user request. The stored data can be called up on display 14, or can be transferred by one of the data transfer means described in the aforesaid U.S. patent application Ser. No. 219,097.

It will thus be understood that the refrigerated fluid sampling apparatus of the invention is multi-functional, i.e., in addition to automatic sampling operations the user can choose to monitor and record data relating to a given fluid condition and/or fluid flow related variables. The various independent or combined operation modes can be effected by user input via keypad 13 to the microprocessor of the apparatus.

In a preferred embodiment, the apparatus according to the invention is adapted to be connected to an external AC power source. If desired, a rechargeable battery such as a gel lead acid battery may be connected to the apparatus as a back-up power source in case of AC power failure.

In addition to a microprocessor, the computer control means according to the invention comprises program storage memory, preferably in the form of firmware comprising FLASH memory which permits software enhancements without replacing E-PROM chips. In addition to program storage memory, the computer control means is also provided with data storage memory in the form of random access memory (RAM) which stores specific details of operation set by the user and records data relating to sampling operations, sample temperatures, fluid flow, fluid condition(s), and/or other data. The RAM is backed-up by its own battery, e.g., a lithium battery, so that data will remain stored therein even when the overall power source of the apparatus is turned off.

The program storage memory is adapted to implement all of the functions required to read and process data for the thermal control system and the sampling control system of the invention as described below. The program storage memory also includes interface programming which allows the microprocessor to control the keypad 13, the display 14, the real-time clock, and to access the active interface devices including any external devices connected with the apparatus.

In one preferred embodiment, the program storage memory may include flow measuring programming which allows the microprocessor to calculate the fluid depth, flow rate, velocity, and other fluid flow-related variables on the basis of processed signals received from a sensor which may be selectively connected with one of the external connectors 16. The programming includes depth vs. flow equations which characterize the relationship between the "head" and flow rate for various types and sizes of fluid flow restricting devices. Also included are equations (e.g., the Manning Equation) for calculating flow variables on the basis of sensor inputs directly from various shaped channels, such as round pipes, U channels, rectangular channels, and trapezoidal channels. Floating point math algorithms are provided to enable the microprocessor to perform high precision mathematical operations required to accurately calculate the values of fluid flow-related variables. Such fluid flow-related variables include the fluid depth which is calculated from the output of a selected flow sensor, and the fluid flow rate which is calculated from the measured fluid depth. Algorithms are included for performing addition, subtraction, multiplication, division, exponentiations, logarithms and trigonometry functions to a precision equivalent to over four significant FIG.

Also in a preferred embodiment, the program storage memory includes fluid condition monitoring programming in the form of firmware which allows the microprocessor to calculate the values of a given fluid condition(s) on the basis of processed signals received from a fluid condition sensor having suitable interface means which may be selectively connected to one of the external connectors 16.

The data storage memory of the computer control means is preferably provided in the form of random access memory (RAM) which stores specific operational parameters set by the user, and stores data during sampling operations and other operations. Parameters which may be set by the user include trip points based on high and/or low fluid condition levels (e.g., pH levels or water level) which trigger sampling apparatus operations. A variety of other parameters which may be input by the user, depending on the types of external equipment selectively connected to the apparatus via external connectors 16, include fluid flow and fluid level, as well as selection of a primary device or channel configuration. The user may also select parameters for monitoring fluid conditions such as pH, temperature, ORP, rainfall, conductivity, dissolved oxygen, etc., as well as other parameters which will become apparent from the description below.

The invention contemplates that the computer control means be programmed to selectively prompt the user, via a series of menu screens displayed on display 14, to enter various desired parameters via keypad 13. In addition to user-programmed entries, all data collected during operation is stored in RAM.

Top-Mounted Compressor Assembly

Figure 2:
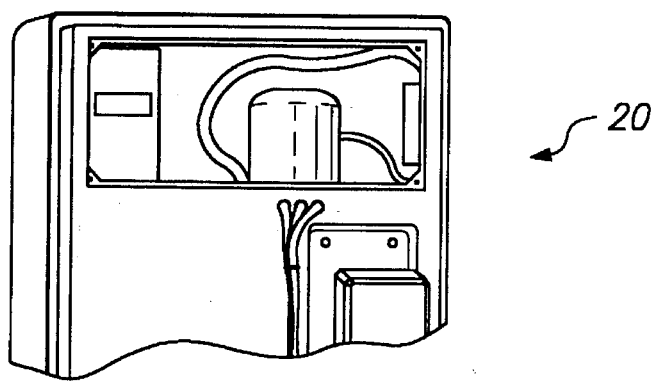
FIG. 2 is a rear view of the top-mounted compressor assembly of the refrigerated fluid sampling apparatus according to the invention.

In accordance with a principal feature of the refrigerated sampling apparatus according to the invention, the compressor assembly 20, including compressor 27, compressor heater 22, condenser 28, and condenser fan 29 (FIG. 5), is mounted in an upper portion of housing or cabinet 1, rearwardly of controller unit 3, as shown in FIG. 1 and 2. Because the compressor assembly 20 is mounted in an upper portion of cabinet 1 which is above the sampler compartment 2, compressor-generated heat is vented away from the cooled compartment rather than up and around the compartment as in known refrigerated sampler arrangements.

The top-mounted compressor assembly 20 is also protected from the corrosive effects of waste water by-products, such as chlorine and hydrogen sulfide, and other corrosive substances typically found on or near floor or ground surfaces. In addition, top-mounting of compressor assembly 20 makes servicing more convenient.

To afford corrosion protection for the refrigeration lines of the apparatus, it is contemplated that the lines be coated with a chemical-resistant material.

Thermal Control System

Figures 5, 5A:
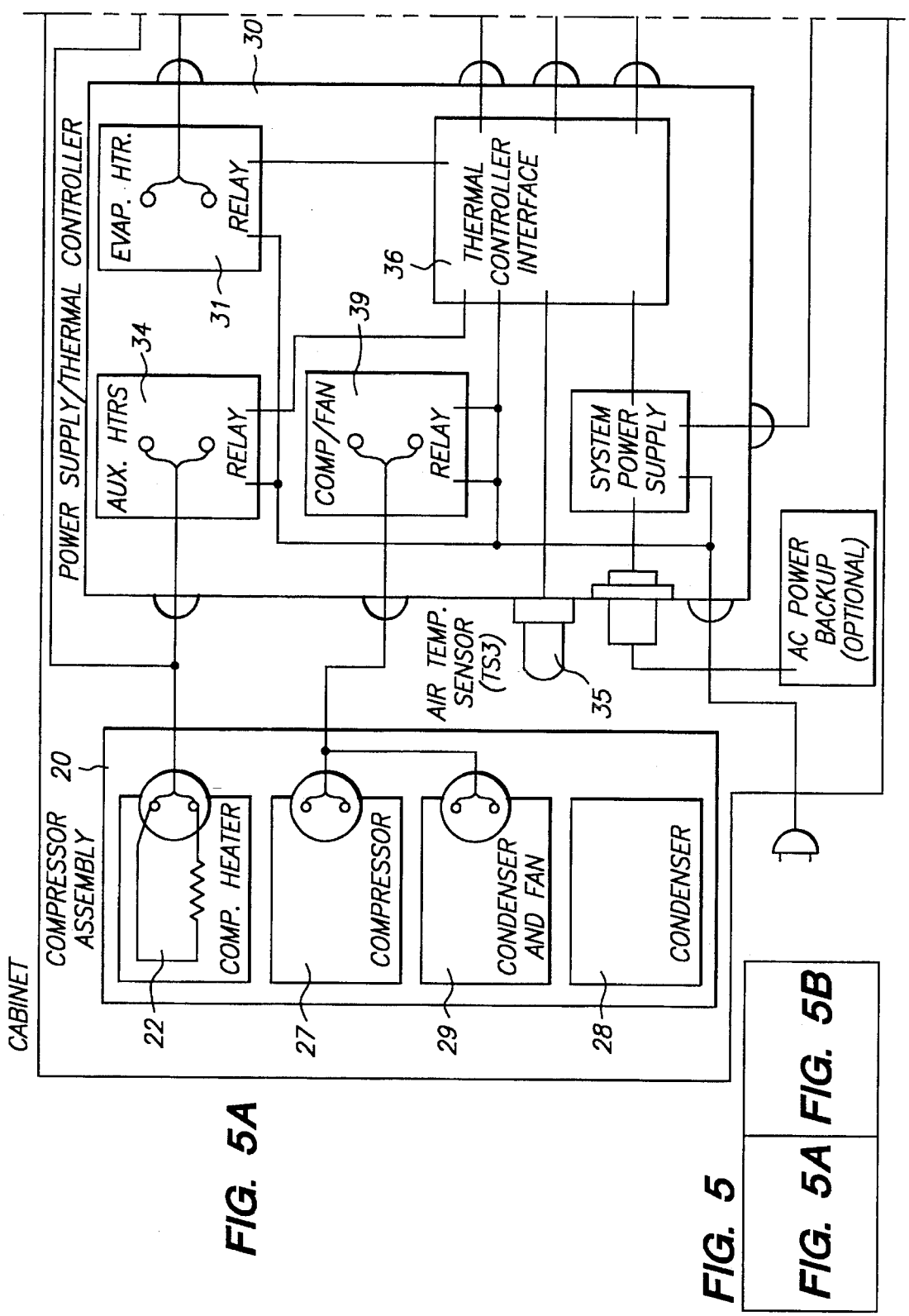
FIG. 5 is a block diagram showing the various components of the apparatus according to the invention as interconnected with the controller unit of the apparatus.
Figure 5B:
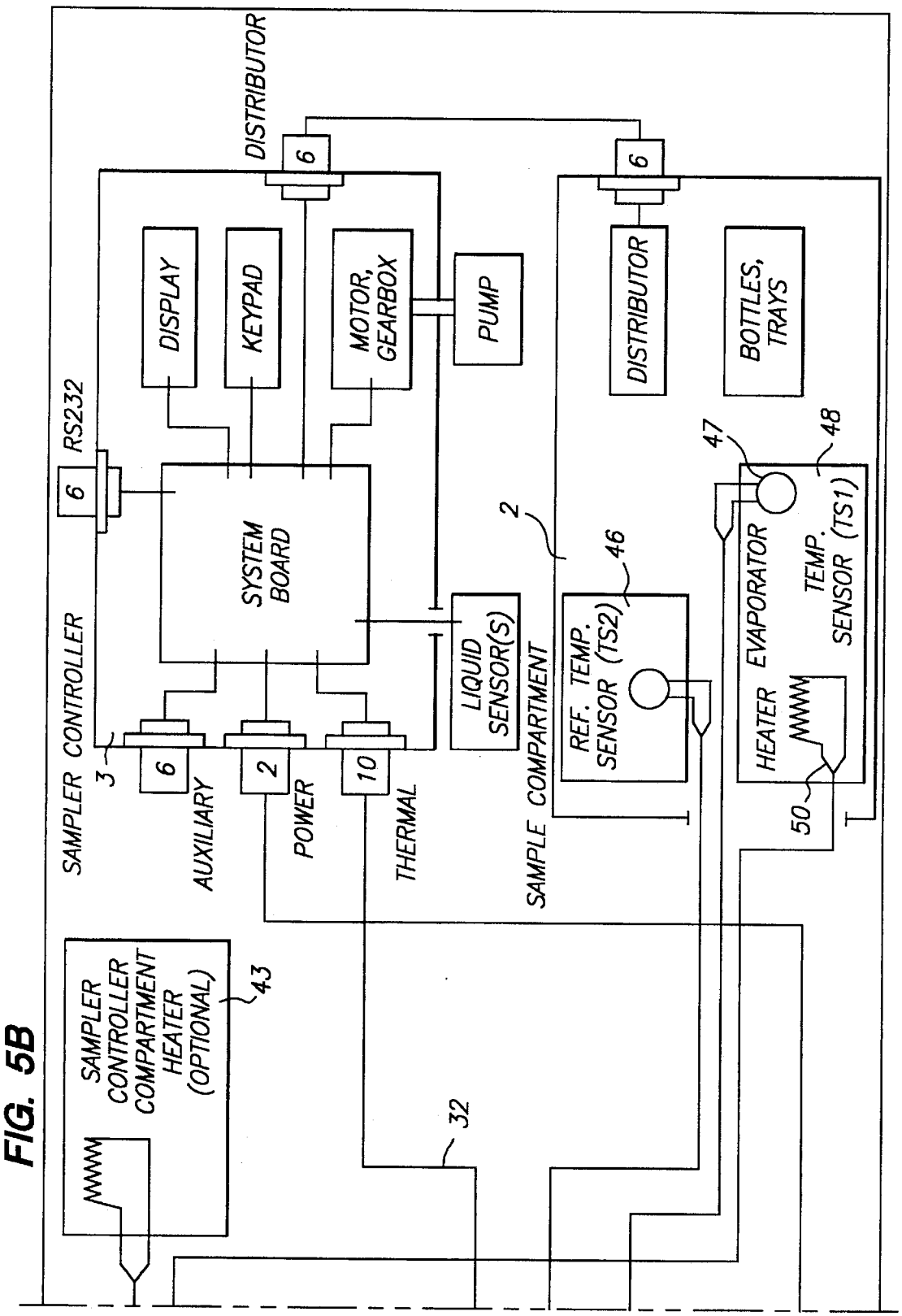

The novel thermal control system for optimizing compressor operation in accordance with the invention will now be described with reference to FIGS. 5–8. Shown in the block diagram of FIG. 5 is the controller unit 3, a thermal controller system 30, a compressor assembly 20, and the sample compartment 2. The microprocessor of controller unit 3 is connected to thermal controller system 30 via conductor 32 so as to receive signals from thermal controller 30 as well as to send signals thereto to control thermal components.

A central component of thermal controller 30 is the controller interface circuitry 36, which transmits signals between the microprocessor of controller unit 3 and various components of the thermal control system. Thermal controller 30 further comprises a compressor and fan control relay 39, an evaporator heater control relay 31, and a compressor heater and sampler controller compartment heater control relay 34. Thermal controller interface circuitry 36 is connected to an ambient temperature sensor 35, a reference temperature sensor 46, and an evaporator temperature sensor 47, so as to receive signals therefrom indicating the temperatures at each given location. Thermal controller interface circuitry 36 is further connected to compressor and fan control relay 39 so as to control operation of a compressor 27 and condenser fan 29. The interface circuitry 36 is also connected to the evaporator heater control relay 31 to control operation of an evaporator heater 50, as well as to the compressor heater and sampler controller compartment heater control relay 34 to control operation of a compressor heater 22 and a sampler controller compartment heater 43.

The sampler controller compartment heater 43 provides heat to the upper portion of cabinet 1 in which controller unit 3 is housed, so as to prevent fluid from freezing in a pump 8 (described below) while prolonging the life of various pump components.

In operation, the novel thermal control system of the invention controls the temperature of fluid samples deposited within the sample compartment 2 of the apparatus to a setpoint temperature, ±1 degree Celsius, within a predetermined setpoint temperature range, over an ambient temperature range of −40 to +50 degrees Celsius.

The thermal control system controls the temperature within the sample compartment 2 in a manner which optimizes compressor operation relative to less efficient known arrangements. In some types of known thermal control systems, an air sensing temperature sensor is employed which has only a minimal thermal mass and which is comprised only of the minimal packaging necessary for environmental protection of the sensor. Such air sensing temperature sensors closely follow the air temperature within the sample compartment, so that they fail to accurately represent the actual temperature of the sample. Following the air temperature so closely also causes frequent compressor or heater starts in order to maintain temperature control, resulting in greater mechanical wear on these parts.

Figure 8:
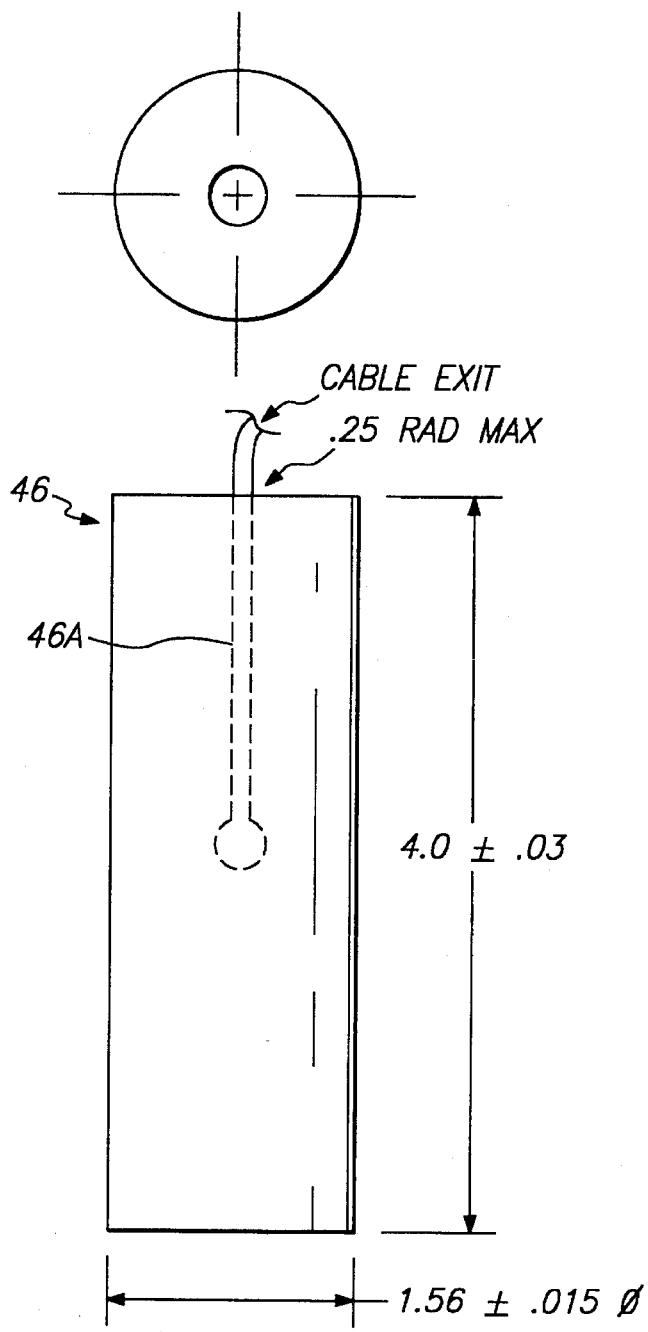
FIG. 8 shows an elevational view of a reference temperature sensor for use in the thermal control system of the invention.

Unlike the foregoing known sensors, the reference temperature sensor 46 of the invention, which senses the temperature of sample compartment 3, comprises a thermistor embedded in a thermal mass, with the thermal mass being sized to simulate a predetermined quantity of water, such as preferably 150 ml (or at least substantially 25 ml). With reference to FIG. 8, the thermistor 46A comprises an ultra-precision Negative Temperature Coefficient ("NTC") thermistor. Unlike the resistance/temperature characteristic of most metals, the NTC thermistor decreases in resistance as body temperature increases. Further, the resistance/temperature characteristic of the NTC thermistor is nonlinear.

The construction and size of reference temperature sensor 46 is selected so as to simulate a glass beaker holding 150 ml of water. Sensor 46 is injection molded of a material which is not susceptible to rust, corrosion and the like, such as Valox 310 SEO, a plastic material. As shown in FIG. 8, thermistor 46A is embedded in approximately the center of the thermal mass. The size of sensor 46 is preferably approximately four inches long (±0.03 inch) with a diameter of approximately 1.56 inches (±0.015 inch).

The novel sensor arrangement introduces a thermal time constant into the system which effectively enhances thermal control relative to known sensors by minimizing the number of compressor starts so as to maximize compressor life and by affording sample compartment 2 temperature recordings which are more representative of actual sample temperature. Further, because sensor 46 has a thermistor-type construction, it provides the advantages of an environmentally sound package, and relatively simple, low cost drive circuitry. Further, sensor 46 is relatively inexpensive, has relatively high resistance values which substantially eliminate lead resistance problems, and has a relatively fast response.

To control the temperature in sample compartment 2, temperature information from reference temperature sensor 46 is used by the thermal controller system to control operation of both compressor assembly 20 and evaporator heater 50. The system uses temperature information from evaporator temperature sensor 47 to control the operation of the evaporator defrost cycle, while using temperature information from ambient temperature sensor 35 to control operation of compressor heater 22 and sampler controller compartment heater 43.

Figure 6A:
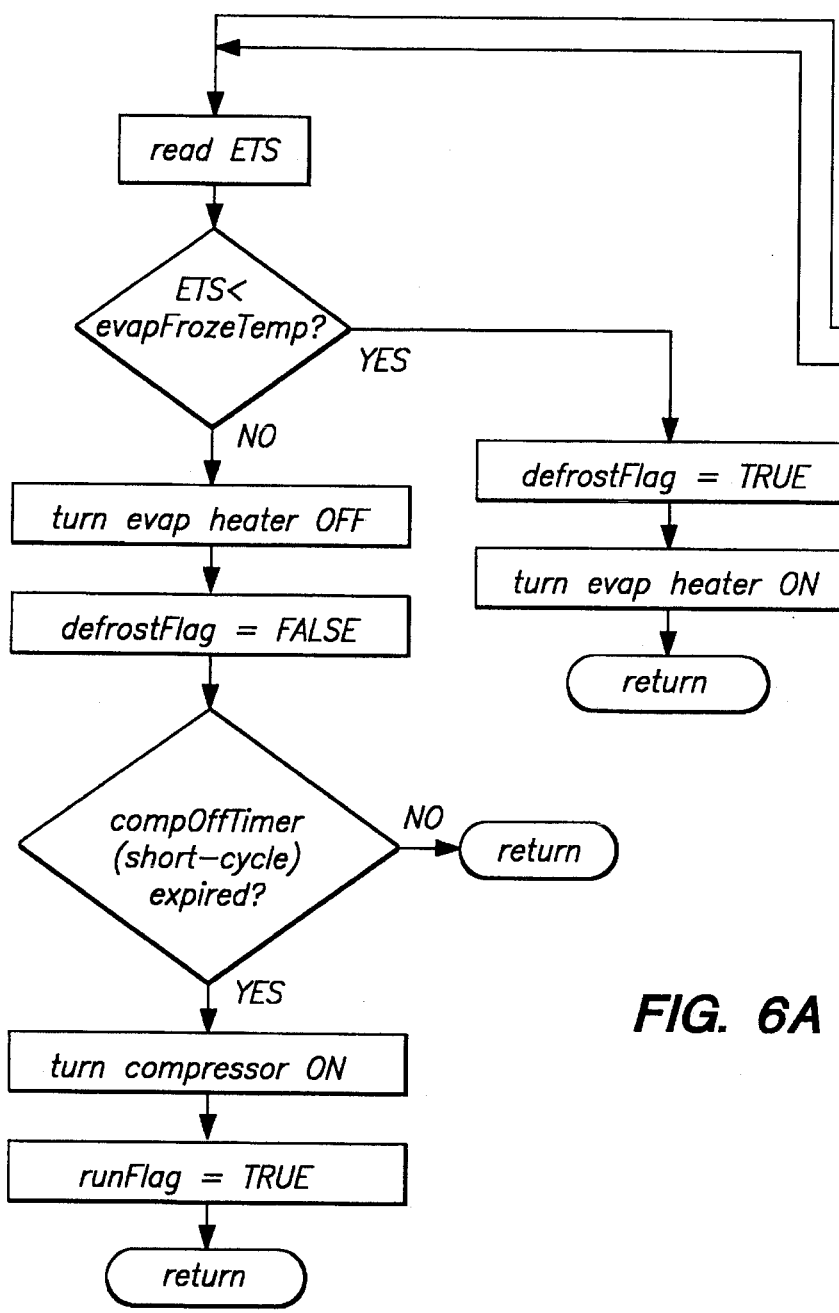
FIG. 6 is a flow chart showing operational sequences of the thermal control system of the apparatus according to the invention.
Figure 6B:
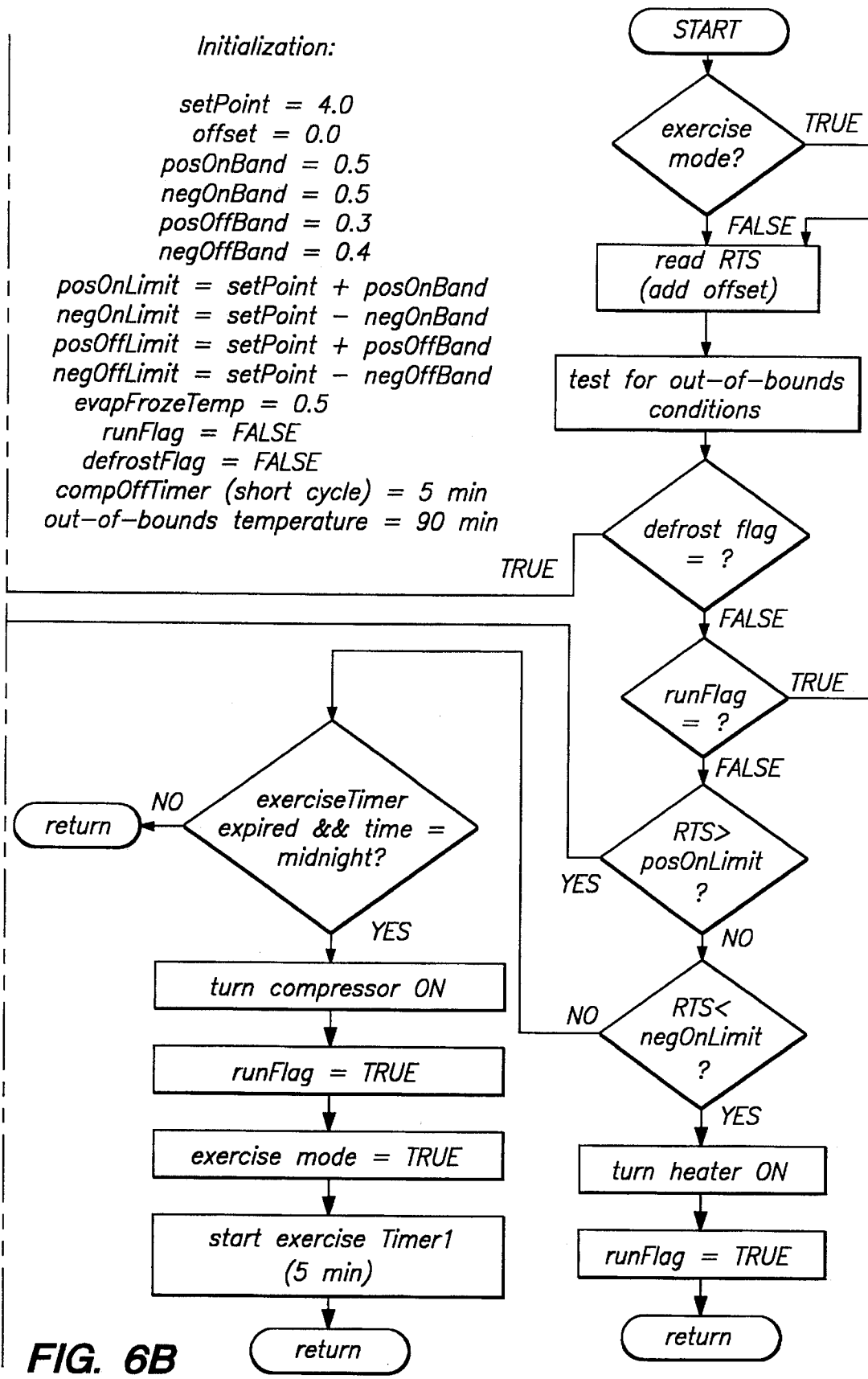
Figure 6C:
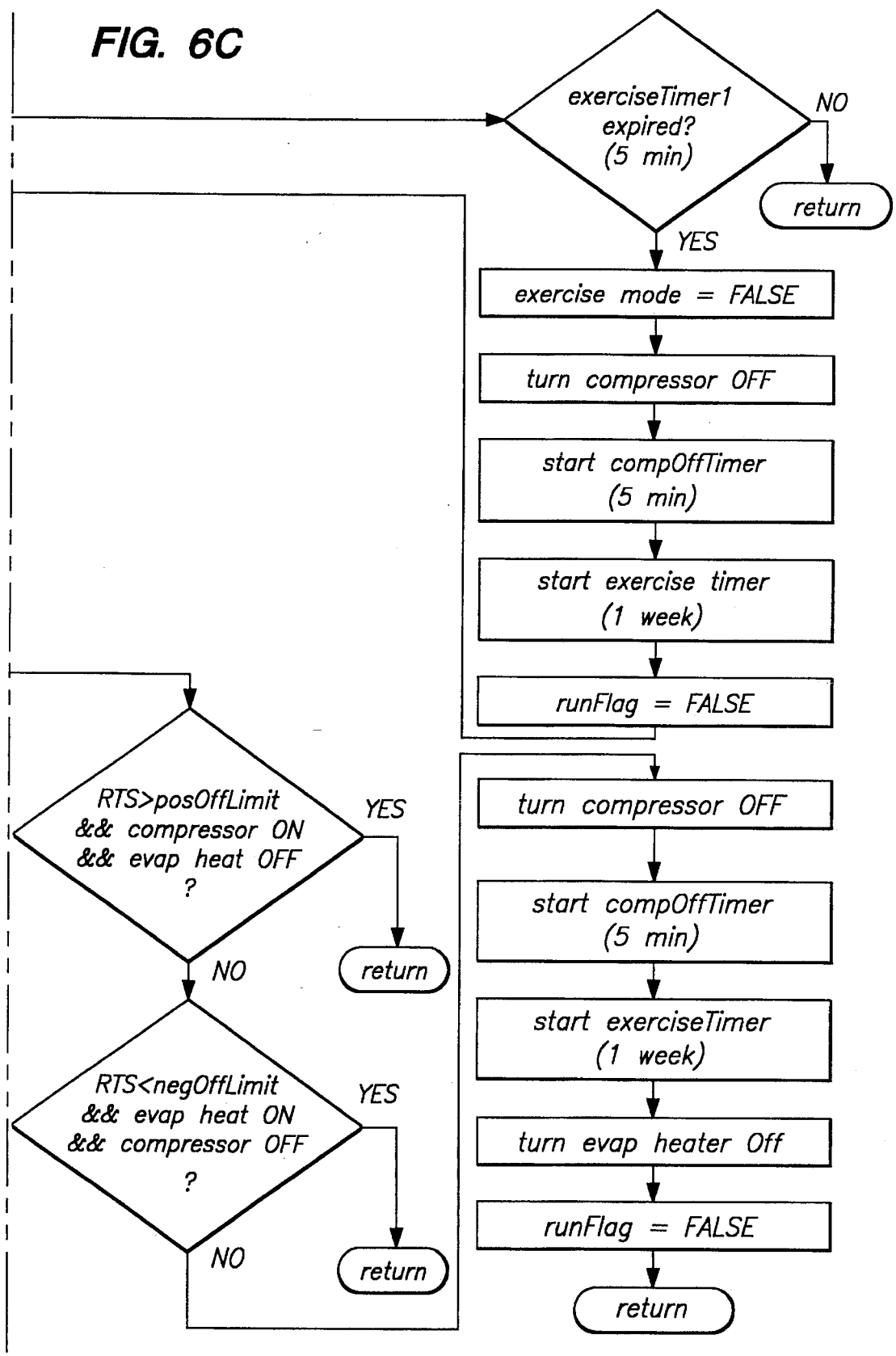

With reference to FIG. 6, the operation of the thermal control system will be described with respect to the thermal control algorithm or subroutine used to control temperature within sample compartment 2 to a setpoint temperature, ±1 degree C. Generally, the system first determines if it is in the exercise mode. The exercise mode is a unique feature of the invention in which compressor assembly 20 is operated or exercised during relatively extensive periods of non-use, such as when the apparatus is being employed in cold ambient temperature conditions. As shown in the upper right portion of FIG. 6, if the exercise mode is determined to be active, the subroutine returns.

Next, the system reads the reference temperature sensor 46 and the calibration offset is added. A check is then performed for out-of-bound temperatures, and if such a temperature is detected, a fault is annunciated. The system then checks to determine if the defrost cycle is active, i.e., whether the evaporator heater 50 is ON to melt ice on evaporator 48. If the defrost cycle is active, the system reads the evaporator temperature sensor 47 and a decision is made to turn OFF evaporator heater 50. It will be understood that if the defrost cycle is active, operation of compressor assembly 20 is not possible and the subroutine returns.

The system next checks to determine if either compressor assembly 20 or evaporator heater 50 is ON. If either compressor assembly 20 or evaporator heater 50 is determined to be ON, compressor assembly 20 or evaporator heater 50 is turned OFF only when the temperature of sample compartment 2 traverses a predetermined setpoint temperature. If compressor assembly 20 is thus turned OFF, an exercise timer (FIG. 6) is activated to monitor periods of non-use of compressor assembly 20 so that the above-described exercise mode may be initiated when necessary.

Another novel feature of the thermal control system of the invention is a means for preventing short cycling of compressor assembly 20. A short cycle timer, i.e., "compOff-Timer" in FIG. 6, is activated to prevent compressor assembly 20 from being turned ON within a predetermined period of time from the last operation of compressor assembly 20. By way of example, the predetermined period of time may be five minutes, as shown in FIG. 6. Short cycling of compressor assembly 20, which could mechanically damage the compressor, is thus prevented.

If compressor assembly 20 or evaporator heater 50 are found OFF, the system performs a check to determine if either component should be turned ON. If operation of compressor assembly 20 is called for, the system reads evaporator temperature sensor 47 and checks to determine whether defrost cycle operation is required. If operation of the defrost cycle is required, evaporator heater 50 is turned ON and the subroutine returns. If, on the other hand, the defrost cycle is not required, compressor assembly 20 is turned ON.

As further shown in FIG. 6, if operation of evaporator heater 50 is called for, it is turned ON. If operation of evaporator heater 50 is not called for, the system checks to determine if the exercise timer has expired. If the exercise timer has expired, compressor assembly 20 is turned ON and permitted to operate for a five minute period. If the exercise timer has not expired, the subroutine returns.

With various known thermal control systems, the compressor assembly and evaporator heater must both operate simultaneously in order to sufficiently control the sample compartment temperature when ambient temperatures fall and approach the setpoint temperature of the sample compartment. Unlike such known systems, the apparatus according to the present invention operates as described above such that the compressor assembly 20 and evaporator heater 50 never operate at the same time, thus reducing overall power consumption.

Figure 7:
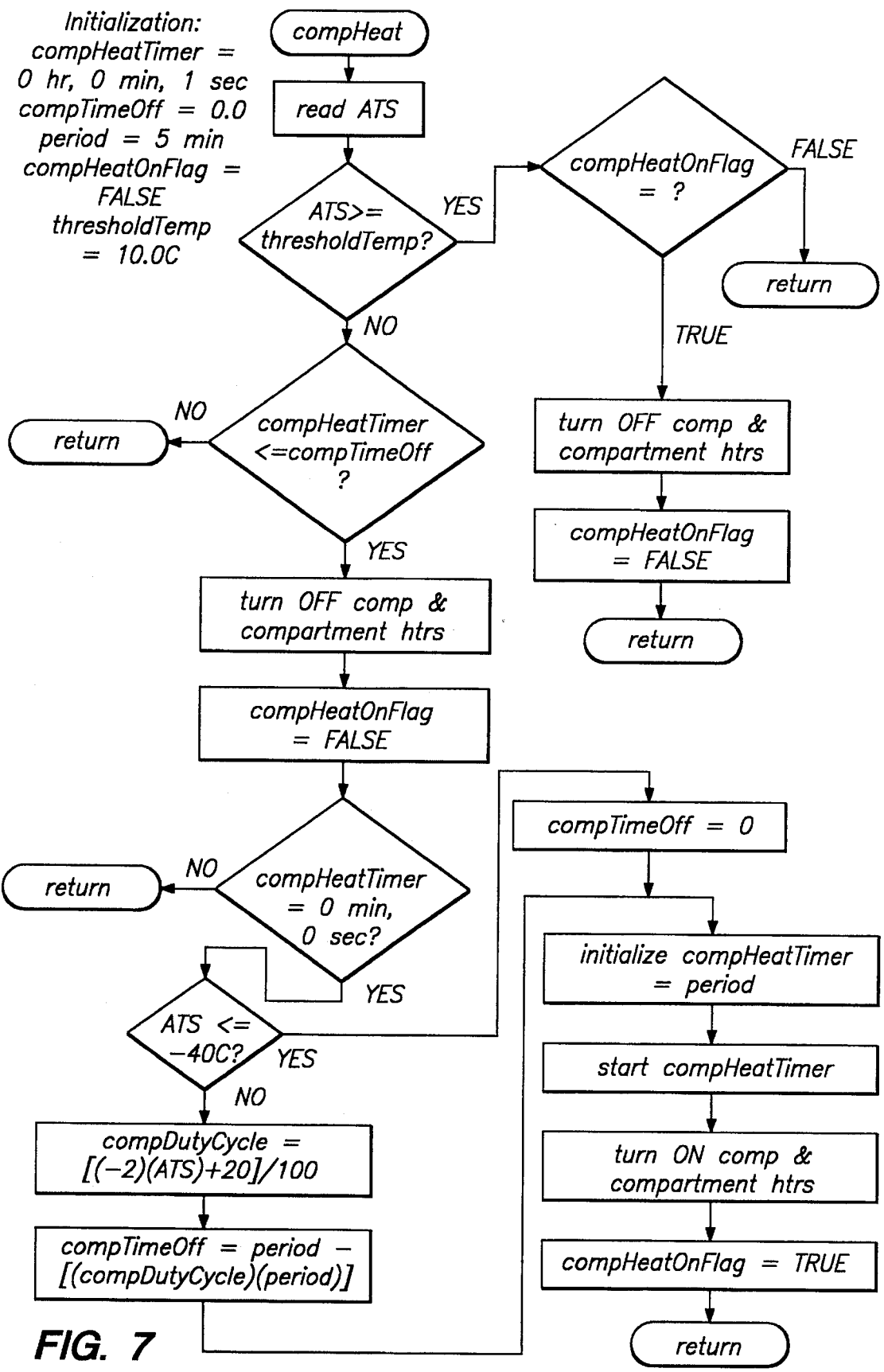
FIG. 7 is a flow chart showing a control algorithm for operation of the compressor heater and sampler controller compartment heater of the invention.

With reference to FIG. 7, there is depicted a control algorithm or subroutine for operation of compressor heater 22 and sampler controller compartment heater 43. Generally, the system reads ambient temperature sensor 35 and if the ambient temperature is greater than a predetermined temperature ("threshold" in FIG. 7), both compressor heater 22 and sampler controller compartment heater 43 are turned OFF. Under this condition, subsequent entries into the subroutine will return. On the other hand, if the system reads ambient temperature sensor 35 and determines that the ambient temperature is below the threshold temperature, a series of steps are initiated as shown in FIG. 7 which modulate the compressor heater 22 and sampler controller compartment heater 43 ON and OFF as a function of ambient temperature. The control equation is as follows:

Modulation Duty Cycle %=[(−2)(ambient temperature)+20]/100

From the above it will be understood that the novel thermal control system of the invention effectively optimizes compressor operation throughout a wide range of ambient temperature conditions, reduces power consumption, and minimizes the mechanical wear to which the compressor is subjected. The system further provides frost-free operation, while ensuring that samples deposited within sample compartment 2 are maintained at a desired constant temperature under harsh ambient temperature conditions.

Sampling Control System

The novel sampling control system according to the invention, which may be used in the above-described refrigerated fluid sampling apparatus as well as in any other suitable automatic fluid sampling apparatus as described below, will now be described with reference to FIG. 9; while the novel constant time, variable volume feature of the sampling control system will be described with reference to FIGS. 10 and 11.

Figure 9:
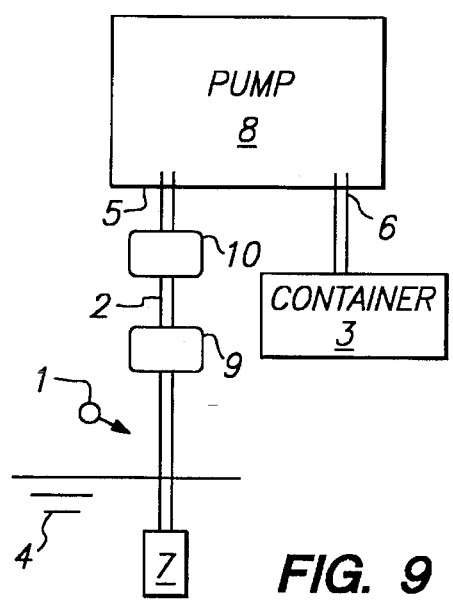
FIG. 9 is a diagrammatic view of various components of the sampling control system according to the invention.

With reference to FIG. 9, the pumping system of the invention preferably includes a reversible, peristaltic, positive displacement pump 8, which may be generally similar to the type described in U.S. Pat. No. 4,660,607 issued in 1987 to Griffith et al. The disclosure of such patent is incorporated herein by reference thereto. The pump 8 may preferably be mounted on a side portion of case 11 of controller unit 3, with the inlet 5 of pump 8 selectively connected to a suitable length of sample intake tubing 1. Provided at the lower intake end of tubing 1 is a weighted strainer 7 which holds the end of the tubing under water and prevents large objects from entering and blocking the tubing. A pair of spaced-apart fluid detection sensors 9 and 10 of the non-wetted, non-contact type are positioned at a portion of tubing 1 proximal the pump inlet 5. The sensors 9 and 10 each generate an output signal when fluid appears in the corresponding portion of tubing 1, which output signals are transmitted to the computer control means of the invention as described in detail below.

Although not shown, a length of tubing extends through pump 8 where it is acted upon by rollers which cause fluid to be drawn upwardly from a fluid source 4 through strainer 7 and intake tubing 1. A length of tubing 6 extends from the pump 8 to a sample container 3, with an electro-mechanical distributor mechanism or sample directing member (not shown) being provided for routing fluid samples to either a plurality of containers 3 or a single container, as desired. The pump 8 is cyclically operated in a reverse purging direction or a forward sample drawing direction depending on signals supplied by processing means incorporated in the computer control means of the invention.

The sampling control system according to the invention uses a statistical model to simulate real-life system and operating characteristics of the pumping system including pump 8. Generally, the sampling control system detects the presence of fluid and determines the delivered (output side) flow rate of the fluid by measuring the average velocity at the intake side of pump 8 by means of sensors 9 and 10. A computer-simulated statistical model, developed by regression analysis based upon data collected through experiments in a simulated environment, is stored in the computer control means of the apparatus, while the real-life system continuously monitors the presence of fluid. The simulation model replicates the configuration of the real-life pumping system both on a macro and a micro level. After a number of simulation runs, the analytical model approximates and aids in the interpretation of the simulation model and ultimately, of the real-world system itself.

Fluid volume for a full conduit flow is the product of flow rate and time. To obtain an accurate sample volume, the flow rate must be known or approximated as precisely as possible so that the appropriate amount of pumping time can be ascertained. Flow rate is the product of the fluid velocity and the cross sectional area of a conduit. To approximate flow rate accurately, the cross sectional area must be controlled to minimize variation, so that estimated fluid velocity can be used directly to estimate flow rate.

The invention contemplates two different methods of estimating the flow rate at the output of pump 8. First, on the basis of the average intake velocity between the sensors 9 and 10, the intake flow rate and correction factor is calculated so as to predict the delivered flow rate at the output side of the pumping system, and ultimately to determine the productive pumping time for a desired sample volume. Secondly, the average fluid velocity at the intake side of pump 8 once fluid is detected by a sensor is used to calculate the intake flow rate. The intake flow rate is then used in conjunction with the intake tubing length to calculate the correction factor for predicting the delivered flow rate at the output side of the pumping system. The correction factor for both methods is adjusted if a user chooses to perform a calibration interactively. During pumping operation, fluid presence is continuously sensed and monitored to filter out unproductive time, such as when there is an absence of fluid.

With reference to the two-sensor system shown in FIG. 9, the predetermined distance between sensors 9 and 10 is important because during operation of the peristaltic, positive displacement roller pump 8, velocity distribution of the fluid is rippling. Generally, an appropriate distance between sensors 9 and 10 may be determined on the basis of the following variables and equations:

| | |
|---|---|
| V: | Average velocity of fluid passing through sensors |
| Vmax: | Maximum average velocity of fluid passing through sensors |
| F: | Frequency of pumping system |
| Fmin: | Minimum frequency of pumping system |
| n: | Number of pulses of fluid profile between sensors |
| D: | Distance between sensors |
| Dmin: | Minimum distance required between sensors |
| μ: | True mean velocity |
| σ: | Standard deviation of sampler population |
| X: | Sample mean velocity, i.e., an unbiased estimator of μ, following the distribution $N(\mu, \sigma^2/n)$ |
| Equation (1): | $D = (V/2 \cdot F) \cdot n$ |
| Equation (2): | $Dmin = (n \cdot Vmax)/(2 \cdot Fmin)$ |

To determine the minimum value of D, the values of Vmax and Fmin in a given application are to be used.

Determination of the value of n, which is basically the sample size, i.e., the number of pulses, for estimating the average velocity of fluid passing between sensors, is based on the following.

If the confidence interval is $100(1-\alpha)$ percent, and the unknown parameter of velocity is μ, then the probabilities of each set of inequalities is exactly the same, i.e., $1-\alpha$. Thus:

$$P\left[X - z(\alpha/2)\frac{\sigma}{\sqrt{n}}\right] \leq \mu \leq P\left[X + z(\alpha/2)\frac{\sigma}{\sqrt{n}}\right] = 1 - \alpha$$

where $z(\alpha/2)$ is that $100(1-\alpha/2)$ percentile of the $N(0,1)$ distribution, and n needs to be chosen such that $$h = z(\alpha/2)\frac{\sigma}{\sqrt{n}}$$

Hence, $$n = \frac{\sigma^2[z(\alpha/2)]^2}{h^2}$$

By way of example, if the standard deviation σ is 2, and a confidence level of 95 percent is desired (such that α is 5 percent and thus z(0.025) is 1.96 from the standard normal distribution function) for determining that the estimate is within 1.5 unit of measure of the true but unknown mean yieldμ, then:

n=$2^2 \cdot 1.96^2$=6.8295, i.e., a minimum sample size of 7 will be needed.

The pumping system including pump 8 and related components and operating environment has associated therewith two types of independent variables, i.e., variables relating to the system characteristics and variables relating to the operational attributes. The system-related variables are those inherent in the configuration of the system, including tube bias and pump speed variation. Tube bias is the variation of restitutional power or elasticity of the pump tubing. Pump speed variation is caused by varying conditions associated with the motor, gearbox components, pumping components and applied voltage.

The operational-attributes independent variables, which may be input by a user via keypad 13 in response to prompts, include the intake tubing length, and intake tubing diameter and material. The intake tubing length is the length of tubing 1 between strainer 7 and a fluid sensor.

In accordance with the sampling control system of the invention, regression analysis is used to determine the relationships among variables. Because the actual relationships among variables are unknown and are much too complex to be described by a small set of explanatory variables, a statistical metamodel is developed to characterize primary features. The response variable, correction factor, is treated as a random variable which varies around a mean value which is dependent upon the values of the explanatory variables:

Correction Factor=f(variable 1, variable 2, etc.)

Various forms of mathematical models may be used to fit the data from experimental design so as to represent the correction factor as a function of input variables. The most direct form of mathematical model is the algebraic regression model in which the relationship is represented by a structure which is linear in the regressor variables, and using the original raw data (without transformation), e.g.:

$$Y = \beta_o + \sum_{i=1}^{n} \beta_i x_i + \epsilon$$

where $\beta_i$ is the $i^{th}$ coefficient of the regression function;

$\epsilon$ is the random disturbance or random error;

Y is the response variable of cell performance; and $x_i$ is the $i^{th}$ input variable (i.e., from among the independent variables discussed above).

The random error is required because observed responses are subject to variability and cannot be expressed exactly as a linear combination of the predictor variables. The error term may account for only random fluctuation of the responses, predictor variables erroneously omitted from the relationship, incorrect specification of the relationship, or some combination of all these factors. Thus, when the foregoing model is applied to a set of data, the random disturbance accounts for any variation arising apart from the terms supplied by the model.

Where a linear model fails to satisfactorily fit the data, a higher order power term and interactions can be included to form non-linear regression models. Models with linear and second-order term, i.e., quadratic models, may be of the following form:

$$Y = \beta_o + \sum_{i=1}^{n} \beta_i x_i + \sum_{i=1}^{n} \beta_{ii} x_i^2 + \Sigma \beta_{ij} x_i x_j + \epsilon$$

The variable parameters associated with sampling operations include the predetermined volume VD, and the length L of the intake tubing 1. Once pump 8 starts to operate, a timer determines the time from the start of pump operation until the presence of fluid as detected by sensors 9 and 10. The time required for fluid to travel from the strainer 7 to the lower sensor 9 is represented by the variable TSS1. To ensure that the starting position of the fluid is located at strainer 7, a reverse pumping action or pre-purge may be necessary. Further, the time lag between the end of the pre-purge operation and the actual forward pumping action is minimized so that fluid does not re-fill back to the fluid source level. The time required for fluid to travel from sensor 9 to sensor 10 is represented by the variable TS12.

Because pump 8 may fail to draw fluid in a forward direction due to abnormal operating conditions, a failure time-out scheme is provided which is based on the intake tubing length and the predicted minimum flow rate. The average flow rate (FRSS1) at the input side of pump 8 can be calculated from the length of the intake tubing and TSS1. Likewise, the average flow rate (FRS12) can be calculated from the distance between sensors 9 and 10. To determine the length of time required (TPP) for pump 8 to operate to deliver a desired volume, starting after the fluid reaches sensor 10, the pre-selected volume VD is divided by the output flow rate of pump 8 (FROUT). Where an appropriate time delay is allocated after a forward pumping, there is no need in the scheme for deducting the fluid between sensor 10 to fluid container 3. However, the time it takes for fluid to travel from sensor 10 to container 3 must be determined by measuring the volume between sensor 10 and container 3 and then dividing same by FROUT. Thus:

$$TPP = VD/FROUT + TS2D$$

The output flow rate FROUT can be determined either by using FRSS1 with a correction factor COMP, or by using FRS12 with a correction factor CF, as follows:

$$FROUT = CF \cdot FRS12$$

or $$FROUT = COMP \cdot FRSS1$$

Both CF and COMP are represented by analytical regression models with explanatory variables. By way of example, the following regression model may be used:

$$COMP = \beta_o + \beta_1 \cdot LIT + \beta_{11} \cdot LIT \cdot FRSS1 + \beta_2 \cdot LIT^2$$

where LIT is the length of intake tubing 1.

The processing means determines the rate of fluid flow and the time the pump must operate to fill all the tubing plus a desired sample volume, on the basis of signals from a fluid detection sensor disposed upstream of the pump 8, and user programmed data relating to the tubing 1.

Figure 11:
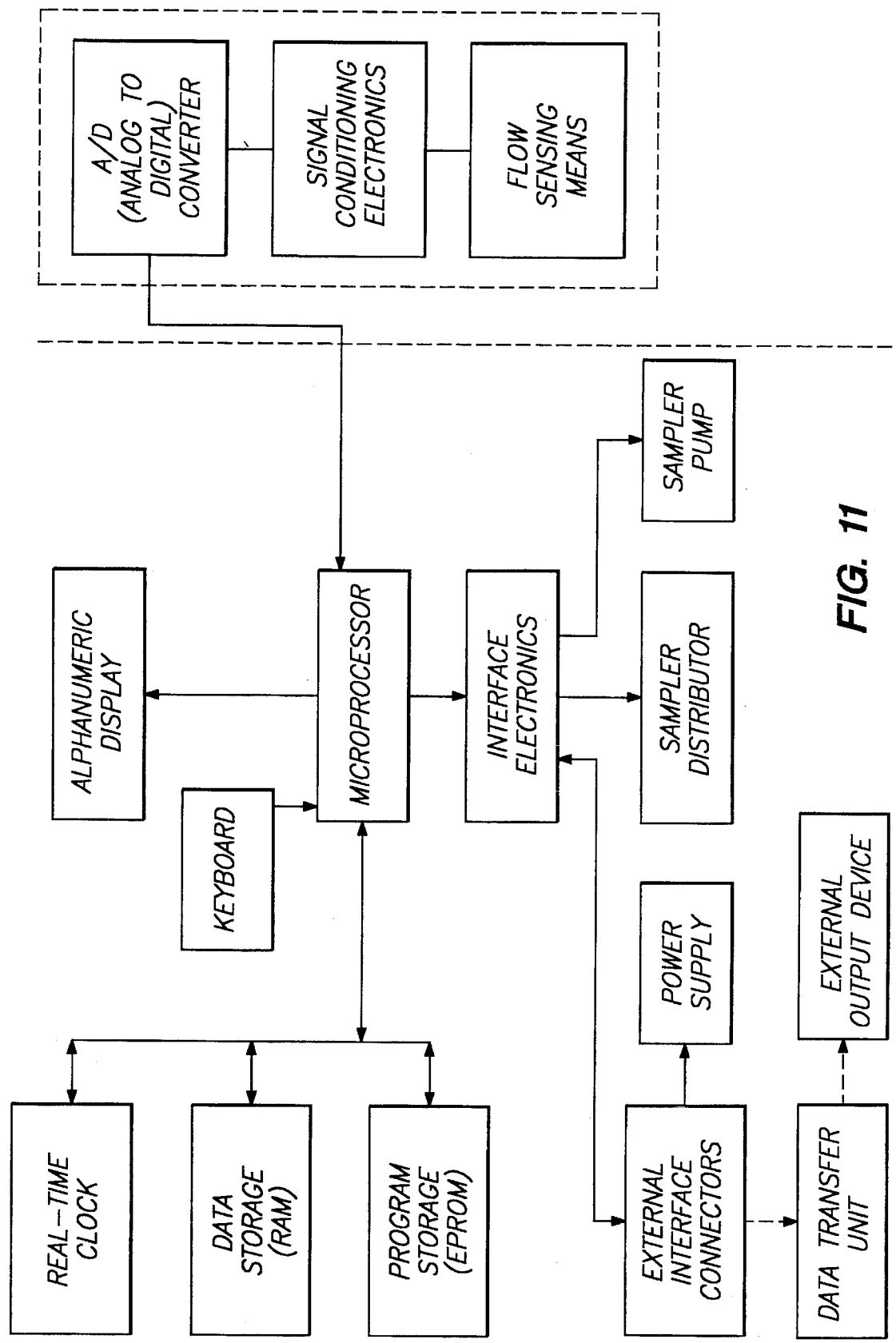
FIG. 11 is a block diagram generally illustrating an automatic fluid sampling apparatus in which the sampling control system according to the invention may be incorporated.

It will be understood that the above-described sampling control system according to the invention is not restricted for use in a refrigerated fluid sampling apparatus such as described herein, and may be employed in any suitable automatic fluid sampling apparatus having computer control means including a microprocessor, program storage memory and data storage memory, such as the system shown diagrammatically in FIG. 11, which may optionally also include flow sensing means as shown. By way of example, the sampling control system according to the invention can be used in the sampling apparatus discussed in the aforesaid U.S. Pat. No. 5,172,332 or U.S. Pat. No. 5,091,863.

Constant Time, Variable Volume Sampling

The foregoing sampling control system according to the invention, by providing for accurate delivery of desired fluid sample volumes, renders the invention capable of providing the novel feature of automatic constant time, variable volume sampling, which will be described with reference to FIGS. 10 and 11. It will be understood, however, that the sampling control system according to the invention may also be used for variable time, constant volume sampling, as well as any other desired sampling mode.

The constant time, variable volume feature of the invention may be incorporated in any suitable fluid sampling apparatus or system having the following features: (i) computer control means including a microprocessor, data storage memory (RAM), and program storage memory (e.g., EPROM); and (ii) the sampling control system according to the invention as described above. Also required is flow measuring means, which may take the form of a separate flow meter connected with an external connector of an automatic sampler, or which may comprise an integral part of a combined apparatus such as disclosed in U.S. Pat. No. 5,091,863. The general features of one exemplary apparatus or system in which the constant time, variable volume feature may be incorporated are shown in the box diagram of FIG. 11.

Figure 10:
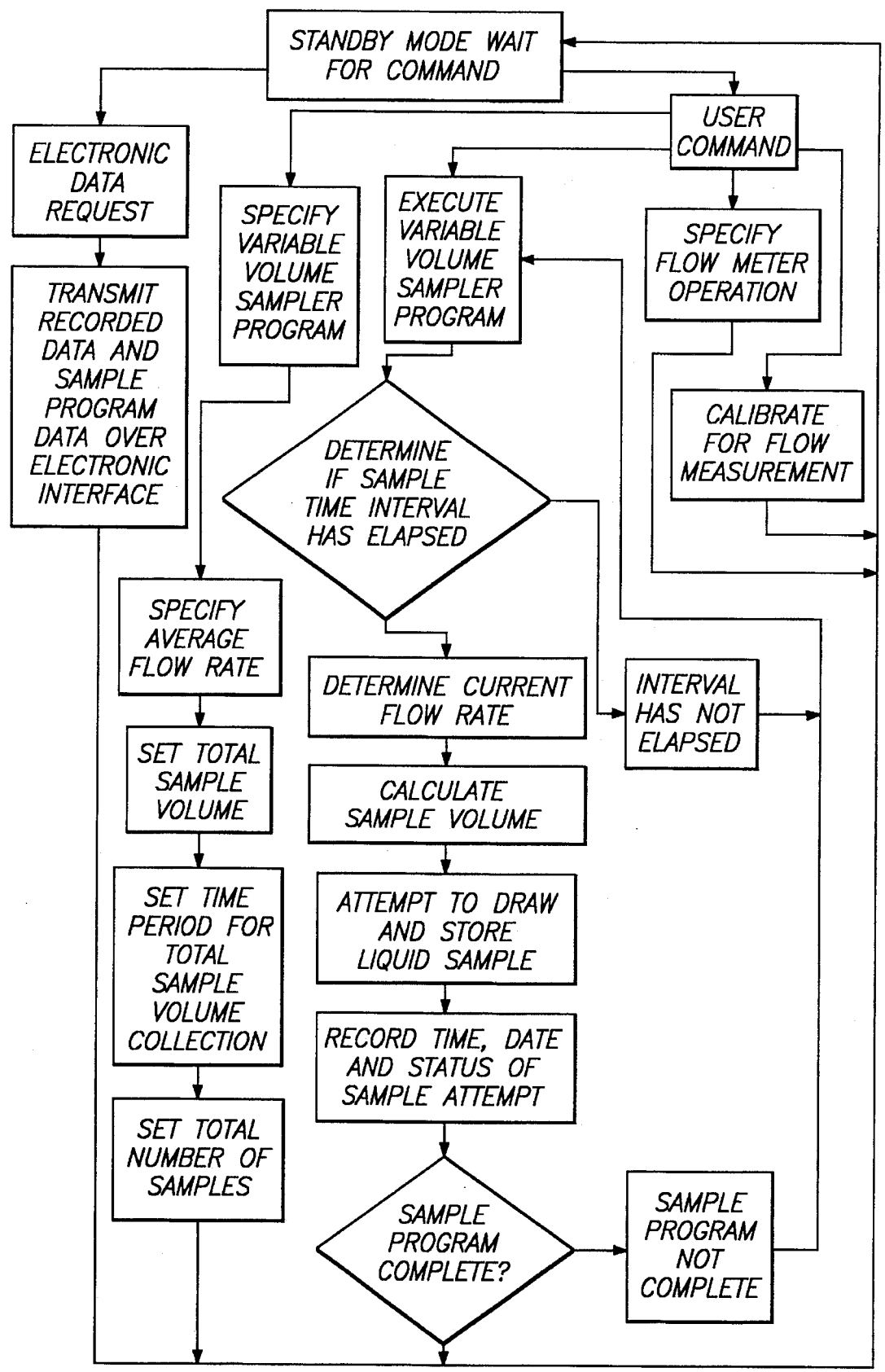
FIG. 10 is a flow chart showing operational sequences of the constant time, variable volume sampling control feature of the invention.

As shown in FIG. 10, the constant time, variable volume sampling program parameters to be input by the user via keypad 13 and stored in RAM include: the average flow rate of the fluid discharge or stream to be sampled; the total sample volume to be collected; the period of time in which the total volume is to be collected; and the total number of samples desired. The invention contemplates that the microprocessor be programmed to sequentially prompt the user (via display 14) to enter these and other desired parameters via keypad 13.

The foregoing sampling program parameters input by the user, together with the above-described sampling control system according to the invention which accurately delivers any desired predetermined sample volume by predicting the delivered flow rate of fluid, provide the system with the ability to vary sample volume in proportion to flow rate on the basis of the following general algorithm, which is stored in the program storage memory of the apparatus:

1. Calculate the average volume per sample as follows:
   Average Volume=(Total Volume)/(Total Number of Samples)
2. Calculate the sample volume per unit flow rate as follows:
   Volume Per Unit of Flow=(Average Volume)/(Average Flow Rate)

When it is time to sample, the volume of the sample is determined as follows:
   Volume of Sample=(Volume Per Unit of Flow)·(How Rate).

On the basis of the foregoing algorithm and user-input parameters, the microprocessor of the apparatus or system controls the length of time pump 8 is intermittently operated to sequentially deliver flow-proportional sample volumes based on the flow rate at the output side of pump 8 as predicted by the above-described sampling control system. The collected sample volumes will thus vary in volume in proportion to the flow rate of the fluid stream or discharge, with samples being collected at regular time intervals throughout the total sample collection time period set by the user. This feature of the invention is particularly useful where a discharge permit requires that samples be collected on a constant time, variable volume basis, or where it is desired to collect samples at regular time intervals with sample volumes varying in proportion to flow.

From all of the foregoing it will be understood that the novel features of the invention are as follows. First, the invention provides a refrigerated fluid sampling apparatus as a self-contained unit which reliably maintains sample temperatures throughout a wide range of ambient temperature conditions. The novel features of the refrigerated fluid sampling apparatus according to the invention include the top-mounted compressor arrangement which maximizes cooling efficiency while ensuring corrosion protection, and the thermal control system which accurately monitors sample temperatures while optimizing compressor operation and prolonging compressor life. A further novel feature of the invention is the sample volume control system which predicts the delivered flow rate of fluid so as to accurately deliver a predetermined amount of sample fluid to a receiving container, which provides for sampling on a "constant time variable volume" basis.

While there have been described hereinabove what are at present considered to be the preferred embodiments of the invention, it will be understood that various modifications may be made therein without departing from the spirit and scope of the invention. The present embodiments are therefore to be considered in all respects as illustrative, and not restrictive. The scope of the invention is indicated by the appended claims rather than by the foregoing description.

What is claimed is:

1. A refrigerated fluid sampling apparatus comprising:

a main housing;

a sample compartment disposed in a lower portion of said main housing;

fluid sampling means, disposed in said main housing, for withdrawing fluid from a fluid channel and delivering fluid samples to said sample compartment;

means for supplying power to said apparatus;

thermal control means for controlling temperatures within said sample compartment, said thermal control means comprising a compressor assembly; and said compressor assembly being disposed in an upper portion of said main housing, above said sample compartment.

2. A refrigerated fluid sampling apparatus according to claim 1, further comprising:

means for controlling said apparatus, said control means comprising a microprocessor connected with said fluid sampling means so as to control automatic sample collection by said fluid sampling means in accordance with one or more modes of operation selected by a user; and said control means being disposed in said upper portion of said main housing.

3. A refrigerated fluid sampling apparatus according to claim 2, wherein:

said sample compartment is substantially rectangular, and extends from substantially the front to the back and from side to side of said lower portion of said main housing;

said control means comprises a controller unit having an operating panel including a keypad and display, said controller unit being disposed in a forward part of said upper portion of said main housing;

said fluid sampling means comprises a pump disposed proximal said controller unit in said forward part of said upper portion of said main housing; and said compressor assembly is disposed in a rear part of said upper portion of said main housing, rearwardly of said controller unit.

4. A refrigerated fluid sampling apparatus according to claim 3, wherein:

said compressor assembly comprises a compressor operably connected with a compressor heater and a condenser fan; and said main housing is fabricated of a weather-resistant material.

5. A refrigerated fluid sampling apparatus according to claim 4, wherein:

said sample compartment has a front opening with a door which sealingly engages said front opening; and said compressor assembly and said controller unit in said upper portion of said main housing are disposed at approximately waist height of a user.

6. A refrigerated fluid sampling apparatus, comprising:

a main housing having a sample compartment disposed therein;

fluid sampling means, disposed in said main housing, for withdrawing fluid from a fluid channel and delivering fluid samples to said sample compartment;

means for supplying power to said apparatus;

means for controlling said apparatus, said control means comprising a microprocessor connected with a thermal control means for controlling temperatures within said sample compartment;

said thermal control means comprising:

thermal controller interface circuitry connected with said control means so as to transmit signals to and from said control means;

a compressor assembly connected with said thermal controller interface circuitry;

first sensor means for sensing temperatures in said sample compartment which are representative of actual sample temperatures, said first sensor means being connected with said thermal controller interface circuitry;

said first sensor means comprising a thermal mass substantially equivalent to a predetermined quantity of water; and signals from said first sensor means being transmitted and processed by said thermal controller interface circuitry and said control means to control operation of said compressor assembly.

7. A refrigerated fluid sampling apparatus according to claim 6, wherein:

said control means further comprises data memory for storing user-selected input parameters including operating mode selection data; and said control means is connected with said fluid sampling means such that said microprocessor controls sample collection by said fluid sampling means in accordance with one or more modes of operation selected by a user.

8. A refrigerated fluid sampling apparatus according to claim 6, wherein:

said first sensor means comprises a sensor casing constructed and dimensioned to simulate a glass beaker holding a quantity of water exceeding substantially 25 ml; and a thermistor is embedded in substantially the center of said thermal mass.

9. A refrigerated fluid sampling apparatus according to claim 8, wherein:

said thermistor is of the Negative Temperature Coefficient type.

10. A refrigerated fluid sampling apparatus according to claim 8, wherein:

said sensor casing is constructed and dimensioned to simulate a glass beaker holding substantially 150 ml of water.

11. A refrigerated fluid sampling apparatus according to claim 6, wherein:

said thermal control means further comprises an evaporator heater connected with said control means via said thermal controller interface circuitry; and signals from said first sensor means, as transmitted and processed by said thermal controller interface circuitry and said control means, control operation of said evaporator heater.

12. A refrigerated fluid sampling apparatus according to claim 6, wherein: said sample compartment is disposed in a lower portion of said main housing; and said compressor assembly is disposed in an upper portion of said main housing.

13. A refrigerated fluid sampling apparatus according to claim 6, wherein:

said control means further comprises program memory which stores a thermal control algorithm for operating said thermal control means; and said microprocessor controls said thermal control means based on said thermal control algorithm to operate said compressor assembly at given time intervals to exercise same during substantial periods of non-use.

14. A refrigerated fluid sampling apparatus according to claim 6, wherein:

said control means further comprises short cycle timing means for controlling operation of said compressor assembly such that said compressor assembly is prevented from being operated within a predetermined interval of time following the last operation of said compressor assembly.

15. A refrigerated fluid sampling apparatus according to claim 13, wherein:

said predetermined interval of time during which said compressor assembly is prevented from being operated by said short cycle timing means is substantially five minutes.

16. A refrigerated fluid sampling apparatus according to claim 10, wherein:

said control means further comprises program memory which stores a thermal control algorithm for operating said thermal control means; and said microprocessor controls said thermal control means based on said thermal control algorithm to prevent simultaneous operation of said compressor assembly and said evaporator heater.

17. A sampling control system for an automatic fluid sampling apparatus having a pump with an inlet adapted to communicate with a supply of fluid to be sampled, and a control means including a microprocessor and program memory, said sampling control system comprising:

sensing means disposed at the input side of said pump for producing at least one signal related to the flow rate of fluid at said input side of said pump;

means for transmitting said at least one signal to said control means;

said microprocessor receives said at least one signal and utilizes said program memory to calculate the flow rate at said input side of said pump;

said program memory stores a statistical regression model for predicting the flow rate at the output side of said pump on the basis of said calculated value of said input side flow rate and a plurality of independent variables associated with operation of said pump; and said program memory stores at least one equation for computing the length of time said pump must operate to deliver a predetermined volume of fluid, based on said predicted flow rate at said output side of said pump.

18. A sampling control system according to claim 17, wherein:

said pump comprises a positive displacement pump;

said sensing means comprises a pair of sensors disposed a predetermined distance apart on intake tubing provided at said input side of said pump; and said at least one signal is related to the fluid velocity between said sensors.

19. A sampling control system according to claim 18, wherein:

said predetermined distance between said pair of sensors is proportional to the average velocity of fluid passing through said sensors and the frequency of the pumping system.

20. A sampling control system according to claim 17, wherein:

said independent variables comprise the tube bias of intake tubing provided at said input side of said pump, and the variation in speed of said pump.

21. A sampling control system according to claim 20, wherein:

said independent variables further comprise user-input operating variables including the suction head, the length of intake tubing provided at said input side of said pump, and the contour of said intake tubing.

22. A sampling control system according to claim 17, wherein:

said pump comprises a positive displacement pump;

said sensing means comprises a sensor disposed on intake tubing provided at said input side of said pump; and said at least one signal is related to the fluid velocity between the fluid inlet end of said intake tubing and said sensor.

23. A sampling control system for an automatic fluid sampling apparatus having a pump with an inlet adapted to communicate with a supply of fluid to be sampled, and a control means including a microprocessor, program memory, and data memory, said sampling control system comprising:

sensing means disposed at the input side of said pump for producing at least one signal related to the flow rate of fluid at said input side of said pump;

means for transmitting said at least one signal to said control means;

said microprocessor receives said at least one signal and utilizes said program memory to calculate the flow rate at said input side of said pump;

said program memory stores a statistical regression model for predicting the flow rate at the output side of said pump on the basis of said calculated value of said input side flow rate and a plurality of independent variables associated with operation of said pump;

said program memory stores at least one equation for computing the length of time said pump must operate to deliver a predetermined volume of fluid, based on said predicted flow rate at said output side of said pump;

said data memory stores user-selected input parameters including at least one known flow rate value associated with a fluid stream or discharge to be sampled;

said program memory further stores an algorithm for calculating the volumes of individual samples to be collected on the basis of said user-selected input parameters;

said microprocessor receives signals related to fluid flow of said fluid stream or discharge from a fluid flow measuring means and calculates individual sample volumes to be collected which are proportional to the flow rate of said fluid stream or discharge, based on said signals related to fluid flow, said user-selected input parameters, and said sample volume algorithm; and said microprocessor controls the length of time said pump is operated to deliver said individual flow proportional sample volumes based on said predicted flow rate at said output side of said pump.

24. A sampling control system according to claim 23, wherein:

said at least one known flow rate value to be input by said user comprises the average flow rate associated with said stream or discharge.

25. A sampling control system according to claim 24, wherein:

said user-selected input parameters further comprise the total time period for sample collection, the total volume of samples to be collected, and the total number of samples to be collected.

26. A sampling control system according to claim 25, wherein:

said algorithm includes equations for calculating the average volume per sample to be collected and the sample volume per unit flow rate.

* * * * *